United States Patent [19]

Tsubakimoto et al.

[11] Patent Number: 4,734,478

[45] Date of Patent: Mar. 29, 1988

[54] WATER ABSORBING AGENT

[75] Inventors: Tsuneo Tsubakimoto; Tadao Shimomura, both of Toyonaka; Yoshio Irie, Nishinomiya; Yoshihiko Masuda, Suita; Kazumasa Kimura, Osaka; Takumi Hatsuda, Suita, all of Japan

[73] Assignee: Nippon Shokubai Kagaku Kogyo Co., Ltd., Osaka, Japan

[21] Appl. No.: 748,820

[22] Filed: Jun. 26, 1985

[30] Foreign Application Priority Data

| Jul. 2, 1984 [JP] | Japan | 59-135330 |
| Oct. 17, 1984 [JP] | Japan | 59-216358 |
| Oct. 23, 1984 [JP] | Japan | 59-221325 |

[51] Int. Cl.$^4$ .............................. C08J 3/24; B01J 20/26
[52] U.S. Cl. .................................. 527/300; 527/311; 527/312; 527/313; 527/314
[58] Field of Search ............... 527/300, 312, 311, 313, 527/314

[56] References Cited

U.S. PATENT DOCUMENTS

| 3,661,815 | 5/1972 | Smith | 527/312 |
| 4,076,663 | 2/1978 | Masuda et al. | 128/284 |
| 4,093,776 | 6/1978 | Aoki et al. | 428/402 |
| 4,282,121 | 8/1981 | Goodrich | 527/312 |
| 4,286,082 | 8/1981 | Tsubakimoto et al. | 526/240 |
| 4,412,036 | 10/1983 | Pedersen et al. | 525/54.26 |

FOREIGN PATENT DOCUMENTS

| 52-14689 | 2/1977 | Japan . |
| 53-15959 | 5/1978 | Japan . |
| 53-156342 | 12/1978 | Japan . |
| 2119384 | 11/1983 | United Kingdom . |

Primary Examiner—Delbert R. Phillips
Assistant Examiner—Nathan M. Nutter
Attorney, Agent, or Firm—Sherman and Shalloway

[57] ABSTRACT

The invention provides [I] a water-absorbing agent composed of a water-absorbing resin powder having the molecular chains near its surface being crosslinked, said powder being obtained by mixing 100 parts by weight of a powder of a carboxyl-containing water-absorbing resin selected from the group consisting of a hydrolyzate of a starch-acrylonitrile graft polymer, a partially neutralized product of a starch-acrylic acid graft polymer, a saponification product of a vinyl acetate-acrylic ester copolymer, a hydrolyzate of an acrylonitrile copolymer, a crosslinked product of a hydrolyzate of an acrylonitrile copolymer, a hydrolyzate of an acrylamide copolymer, a crosslinked product of a hydrolyzate of an acrylamide copolymer, a partially neutralized product of polyacrylic acid, and a crosslinked product of partially neutralized polyacrylic acid with 0.001 to 10 parts by weight of a polyhydric alcohol, 0.01 to 8 parts by weight of a hydrophilic organic solvent and 0 to 8 parts by weight of water, and heating the mixture at a temperature of at least 90° C. to react the water-absorbing resin powder with the polyhydric alcohol; [II] a water-absorbing agent composed of a mixture of the water-absorbing agent [I] with finely divided silica; [III] a water-absorbing agent obtained by pulverizing and granulating a mixture of the water-absorbing agent [I] with an aqueous liquid; and [IV] a water-absorbing agent composed of a mixture of the water-absorbing agent [III] with finely divided silica.

39 Claims, No Drawings

WATER ABSORBING AGENT

This invention relates to water-absorbing agents. More specifically, it relates to water-absorbing agents which do not significantly decrease in flowability nor undergo caking upon moisture absorption, have excellent handlability, contain only a minor proportion of fine particles, have a uniform particle size distribution, thus do not decrease in weight nor pollute the working environment owing to the occurrence of dust, absorb an aqueous substance to a high degree upon contact with it, and have high water retentivity even under pressure.

Attempts have been made to use a waterabsorbing resin as one component of sanitary materials capable of absorbing body fluids, such as sanitary napkins and paper diapers.

The conventional water-absorbing resins all have the serious defect that their speeds of water absorption are slower than cotton-like pulps or paper. For example, when a conventional water-absorbing resin is incorporated in a paper diaper, the amount of water absorbed by the paper diaper is small for some time after the excretion of urine, and the wearer feels unpleasant as a result of contact of urine with the skin, and a long period of time is required until it dries up. Accordingly, various attempts have been made to increase the speed of water absorption.

For example, attempts were made to increase the surface area of the water-absorbing resin by reducing its particle diameter or granulating it or converting it into a scale-like form. Generally, however, when the particle diameter of the water-absorbing resin is reduced, it forms "fish-eyes" upon contact with urine, and this retards the speed of water absorption. Furthermore, when the water-absorbing resin is granulated, a single granule forms a single "fish-eye", and the speed of water absorption becomes slow. By converting the water-absorbing resin into a scale-like form, the speed of water absorption is increased, but is still insufficient. Moreover, there is a restriction on the process of converting the resin into a scale-like form. For example, a scale-like product can be obtained by drying the waterabsorbent resin on a drum dryer. To perform drying on the drum dryer, however, a material to be dried should be a viscous liquid which can adhere to the drum. A gel-like material cannot be dried on it. Accordingly, a restriction will be imposed on the polymerization step, for example, in order to obtain a liquid polymer. Furthermore, scales are necessarily bulky, and large facilities are required for transportation and storage. This is not economical.

Since many of the conventional water-absorbing resins contain a large amount of fine particles which pass through a 100-mesh standard sieve, various problems arise in their utilization. For example, the resins tend to develop dust which pollutes the working environment or decreases the weight of the resins. They have poor mixability and dispersibilty with other materials. They tend to form "fish-eyes" upon contact with a liquid. Since the resin powders have poor flowability, bridge formation and flushing tend to occur in the hopper.

Furthermore, these water-absorbing resins have poor handlability because upon moisture absorption, they tend to decrease in flowability or undergo caking and the powder cannot be uniformly distributed in the making of an absorbent sheet for example, or the powder sticks to the hopper or the molding machine.

The present inventors made extensive investigations in order to solve the aforesaid problems of the conventional water-absorbing resins, and previously found that by crosslinking the surface layer of a specific water-absorbing resin having a carboxyl group with a polyhydric alcohol, there can be obtained a waterabsorbing resin which does not significantly decrease in flowability nor undergo caking upon moisture absorption, has excellent handlability, contains a minor proportion of fine particles, has a uniform particle size distribution, and does not significantly decrease in weight or pollute the working environment by the occurrence of dust (GB No. -2119384A).

It has been desired however to develop a water-absorbing agent having a much higher speed of water absorption and higher water holding property under pressure.

It is an object of this invention therefore to provide a water-absorbing agent which does not significantly decrease in flowability nor undergo caking upon moisture absorption, thus has excellent handlability, contains a minor proportion of fine particles, has a uniform particle size distribution, does not decrease in weight nor pollute the working environment owing to the occurrence of dust, has a high speed of water absorption and high water retentivity even under pressure.

This object of the invention is achieved in accordance with this invention by (I) a water-absorbing agent composed of a water-absorbing resin powder having the molecular chains near its surface being crosslinked, said powder being obtained by mixing 100 parts by weight of a powder of a carboxyl-containing water-absorbing resin selected from the group consisting of a hydrolyzate of a starch-acrylonitrile graft polymer, a partially neutralized product of a starch-acrylic acid graft polymer, a saponification product of a vinyl acetate-acrylic ester copolymer, a hydrolyzate of an acrylonitrile copolymer, a crosslinked product of a hydrolyzate of an acrylonitrile copolymer, a hydrolyzate of an acrylamide copolymer, a crosslinked product of a hydrolyzate of an acrylamide copolymer, a partially neutralized product of polyacrylic acid, and a crosslinked product of partially neutralized polyacrylic acid with 0.001 to 10 parts by weight of a polyhydric alcohol, 0.01 to 8 parts by weight of a hydrophilic organic solvent and 0 to 8 parts by weight of water, and heating the mixture at a temperature of at least 90° C. to react the water-absorbing resin powder with the polyhydric alcohol;

(II) a water-absorbing resin obtained by mixing 100 parts by weight of the water-absorbing agent (I) with 0.01 to 10 parts by weight of finely divided silica;

(III) a water-absorbing agent obtained by adding an aqueous liquid to the water-absorbing agent (I), stirring the mixture, and then pulverizing and granulating it; and (IV) a water-absorbing agent obtained by mixing 100 parts by weight of the water-absorbing resin (III) with 0.01 to 10 parts by weight of finely divided silica.

The water-absorbing resin used in this invention is a carboxyl-containing resin selected from the group consisting of a hydrolyzate of a starchacrylonitrile graft polymer, a partially neutralized product of a starch-acrylic acid graft polymer, a saponification product of a vinyl acetate-acrylic ester copolymer, a hydrolyzate of an acrylonitrile copolymer, a crosslinked product of a hydrolyzate of an acrylonitrile copolymer, a hydrolyzate of an acrylamide copolymer, a crosslinked product of a hydrolyzate of an acrylamide copolymer, a partially neutralized product of polyacrylic acid, and a crosslinked product of partially neutralized polyacrylic acid. These water-absorbing resins are well known in the art. For example, the hydrolyzate of a starch acrylonitrile graft polymer is disclosed in U.S. Pat. No. 3,661,815; the neutralization product of a starch-acrylic acid graft polymer is disclosed in U.S. Pat. No. 4,076,663; the saponification product of a vinyl acetate-acrylic ester copolymer is disclosed in Japanese Laid-Open Patent Publication No. 14689/1977; the hydrolyzate of an acrylonitrile copolymer and the hydrolyzate of an acrylamide copoly disclosed in Japanese Patent Publication No. 15959/1978; the crosslinked products of these hydrolyzates and a self-curable poly(sodium acrylate) obtained by inverse phase suspension-polymerization are disclosed in U.S. Patent No. 4,093,776; and the crosslinked product of partially neutralized polyacrylic acid is disclosed in Japanese Laid-Open Patent Publication No. 84304/1980.

Especially preferred among these water-absorbing resins are alkali metal acrylate-type polymers obtained by copolymerizing 100 parts of an acrylic acid-type monomer composed of 1 to 50 mole % of acrylic acid and 50 to 99 mole % of an alkali metal acrylate and 0 to 5 parts by weight of a crosslinkable monomer in aqueous solution in a monomer concentration of at least 20 % by weight, and drying the resulting gel-like hydrous polymer by heating.

There is no limitation to the amount of the carboxyl groups of the water-absorbing resin. Preferably, at least 0.01 equivalent of carboxyl groups are present per 100 g of the water-absorbing resin. In the case of the partially neutralized polyacrylic acid, the proportion of the unneutralized portion is preferably 1 to 50 mole %.

The shape of the powder of the water-absorbing resins is not particularly restricted, either. For example, it may be a spherical powder obtained by inverse phase suspension polymerization, a scaly powder obtained by drum drying, or an irregularly-shaped powder obtained by pulverizing the resin mass.

Preferably, the water-absorbing resin powder has such a particle size distribution that the proportion of fine particles which pass through a 200-mesh standard sieve is not more than 50 % by weight. If it exceeds 50 % by weight, uniform dispersion of the polyhydric alcohol over the surface of the water-absorbing resin powder is difficult. Moreover, because of the large proportion of the fine particles, the polyhydric alcohol penetrates into the central parts of the particles of the water-absorbing resin, and the proportion of particles in which the crosslinking reaction with the polyhydric alcohol has proceeded to the central part increases. This reduces the performance of the water-absorbing resin.

The polyhydric alcohol is an alcohol having at least 2 hydroxyl groups per molecule. Preferably, the polyhydric alcohol used in this invention is selected from the group consisting of diethylene glycol, triethylene glycol, polyethylene glycol, glycerol, polyglycerol, propylene glycol, diethanolamine, triethanolamine, polyoxypropylene, oxyethylene-oxypropylene block copolymer, sorbitan fatty acid esters, polyoxyethylene sorbitan fatty acid esters, trimethylolpropane, pentaerythritol and sorbitol.

The amount of the polyhydric alcohol used in this invention is 0.001 to 10 parts by weight, preferably 0.01 to 5 parts by weight, per 100 parts by weight of the water-absorbing resin powder. Within this range, a water-absorbing agent having high speed of water absorption is obtained. If it exceeds 10 parts by weight, not only is it economically disadvantageous, but also the proportion of the water-absorbing resin is decreased and the amount of water absorbed decreases. If the amount is less than 0.001 part by weight, no increase in the speed of water absorption is observed even if a long period of time is spent for the heat-treatment.

The hydrophilic organic solvent used in this invention performs the function of promoting the uniform dispersion of the polyhydric alcohol over the surface of the water-soluble resin powder surface and penetration of it in the vicinity of its surface. The hydrophilic organic solvent may be any organic hydrophilic solvent which can be mixed uniformly with alcohols, and does not adversely affect the performance of the water-soluble resin. Examples of the solvent include lower alcohols such as methyl alcohol, ethyl alcohol, n-propyl alcohol, iso-propyl alcohol, n-butyl alcohol, iso-butyl alcohol and t-butyl alcohol; ketones such as acetone; ethers such as dioxane and tetrahydrofuran; amides such as N,N-dimethylformamide; and sulfoxides such as dimethyl sulfoxide. In view of safety and economy, low-boiling lower alcohols, ketones and ethers are preferred. The optimal amount of the hydrophilic organic solvent varies depending upon the type or particle size of the water-absorbing resin powder, and is 0.01 to 8 parts by weight, preferably 0.1 to 6 parts by weight, per 100 parts by weight of the water-absorbing resin powder. If it exceeds 8 parts by weight, mixing or heat-treatment is time-consuming. On the other hand, if the amount of the hydrophilic organic solvent is less than 0.01 part by wight, no effect of adding it is observed.

To promote the penetration of the polyhydric alcohol further into the vicinity of the surface of the water-soluble resin particles, water may be used together. The amount of water used is 0 to 8 parts by weight, preferably 0 to 5 parts by weight, more preferably 0.5 to 4 parts by weight, per 100 parts by weight of the water-absorbing resin powder. If the amount of water used exceeds 8 parts by weight, mixing or heating is time-consuming, and dispersion of the polyhydric alcohol over the surface of the water-absorbing resin powder particles tends to become non-uniform. Furthermore, together with the polyhydric alcohol it penetrates into the central parts of the water-absorbing resin particles, and the crosslinking reaction with the polyhydric alcohol proceeds to their center. This reduces the performance of the water-absorbing resin.

Generally, mixing of the water-absorbing resin powder with the polyhydric alcohol an the hydrophilic organic solvent with or without water in this invention is effected by stirring the water-absorbing resin powder while a mixture of the polyhydric alcohol and the hydrophilic organic solvent or a mixture of the polyhydric alcohol, the hydrophilic orgnanic solvent and water is sprayed or added dropwise to the water-absorbing resin powder. For uniform mixing, mixers having a high mixing power are desirable and ordinary mixers or kneaders may be used. Examples include a cylinderical mixer, a double cone blender, a V-type mixer, a ribbon-type mixer, a screw-type mixer, a fluidizing-type mixer, a rotating disc-type mixer, a gas-current type mixer, a twin armtype kneader, an internal mixer, a muller-type kneader, a roll mixer and a screw-type extruder.

The mixture obtained by mixing the water-absorbing resin with the polyhydric alcohol and the hydrophilic organic solvent with or without water is then heated by using an ordinary dryer or a heating oven, for example a groove-type stirred dryer, a rotating dryer, a disc dryer, a kneading dryer, a fluidized bed dryer, a flash dryer, and an infrared ray dryer. The heating temperature is at least 90° C., preferably 150° to 250° C. If it is less than 90° C., long periods of time are required for the reaction and this is economically disadvantageous. Moreover, with certain types or amounts of the polyhydric alcohol, the crosslinking reaction sometimes does not proceed to an extent sufficient for the exhibition of the effects of this invention. By adjusting the heating temperature to a range of 150° to 250° C., the crosslinking reaction to an extent sufficient for the exhibition of the effects of this invention can be carried out within a short period of time without any likelihood of coloration or degradation of the water-absorbing resin. At high temperatures exceeding 250° C., heat degradation occurs in certain types of the water-absorbing resin.

The water-absorbing agent (I) so obtained has various advantages over the conventional known water-absorbing resins. The water-absorbing agent (I) of this invention can be produced at low cost by a simple industrial method comprising mixing the water-absorbing resin powder with the polyhydric alcohol and the hydrophilic organic solvent with or without water thereby to react the water-absorbing resin powder effectively with the polyhydric alcohol. Furthermore, it has a higher speed of water absorption than the conventional known water-absorbing resins without forming "fish-eyes" of the powder, and surprisingly, has high water retentivity even under pressure.

According to one preferred embodiment of this invention, the water-absorbing agent (II) is obtained by mixing the water-absorbing agent (I) having such excellent properties with finely divided silica. The water-absorbing agent (II) does not significantly decrease in flowability nor undergo caking upon moisture absorption, and has excellent handlability It also retains the excellent properties of the water-absorbing agent (I).

Finely divided silica has silicon dioxide having an average particle diameter of not more than 10 microns as a main component, and includes, for example, "Aerosil 200 (a trade name for a product of Japan Aerosil Co., Ltd.) or "CARAPLEX ®#67"(a trade name for a product of Shionogi & Co., Ltd.).

The amount of the finely divided silica used is 0.01 to 10 parts by weight per 100 parts by weight of the water-absorbing agent (I). If the amount is less than 0.01 part by weight, no effect of adding silica is observed. If it exceeds 10 parts by weight, no effect is obtained corresponding to the amount used, and this is uneconomical.

To obtain the water-absorbing agent (II) by mixing the water-absorbing agent (I) with finely divided silica, ordinary mixing methods and devices may be used, and there is no particular restriction to them.

According to another preferred embodiment of the present invention, the water-absorbing agent (III) is obtained by adding an aqueous liquid to the water-absorbing agent (I), stirring the mixture and then pulverizing and granulating the mixture. The water-absorbing agent (III) has a small proportion of fine particles and a uniform particle size distribution and does not decrease in weight nor pollute the working environment owing to the occurrence of dust. It also retains the excellent properties of the water-absorbing agent (I).

Water alone or a mixture of water with a water-miscible organic solvent is used as the aqueous liquid. The proportion of water in the mixture is preferably at least 50 % by weight. Examples of the water-miscible organic solvent are lower alcohols, lower glycols, monoethers of ethylene glycol and lower alcohols, glycerol and acetone.

A mixture of water or the above mixture with another compound or with a mixture of compounds may also be used. Examples include deodorizing agents, plant growth aids and water-soluble polymers which dissolve in water or the mixture.

Examples of the deodorizing agents include extracts of plants of the family camellia having flavanols or flavonols as deodorizing components, or leaf alcohols. These materials exhibit an excellent deodorizing effect when the resulting water-absorbing agent is used in sanitary articles such as sanitary napkins or paper diapers.

Examples of the plant growth aids include hydrogen peroxide as a source of supply of oxygen effective for the growth of plant roots, and compounds containing nitrogen, phosphorus or potassium, such as ammonium nitrate, urea and potassium phosphate which are fertilizers for plants. The water-absorbing agent (III) which contains such a plant growth aid shows an excellent plant growth promoting effect when used as a water holding agent for agriculture and horticulture.

Examples of the water-soluble polymers include polyacrylic acid, poly(alkali metal acrylates), carboxymethyl cellulose, hydroxyethyl cellulose, polyethylene glycol and polyvinyl alcohol. The use of these water-soluble polymers can desirably increase the mechanical strength of the resulting granular product and makes it easy to handle the water-absorbing agent (III). If the concentration of the water-soluble polymer is too high, the viscosity of the aqueous liquid becomes high and it becomes difficult to prepare and convey the aqueous liquid. The concentration of the water-soluble polymer is usually not more than 10 % by weight.

The amount of the aqueous liquid is 1 to 30 parts by weight per 100 parts by weight of the water-absorbing agent (I). If it is less than 1 part by weight, granulation sometimes becomes insufficient. If it exceeds 30 parts by weight, granules having a large particle diameter tend to form undesirably One preferred means for stirring and mixing the water-absorbing agent (I) and the aqueous liquid is to use a high-speed rotating paddle-type mixer. The high-speed rotating paddle-type mixer is a mixer comprised of a cylindrical vessel and a rotor therein equipped with a plurality of paddles and adapted to rotate at high speeds. It mixes or disperses at least two types of powder, or a powder with or in a liquid. Commercially, it is available under trade names Turburizer and Sand Turbo (both are the products of Hosokawa Micron Co., Ltd.).

The water-absorbing agent (I) and the aqueous liquid may be mixed by continuously or intermittently supplying the water-absorbing agent (I) and the aqueous liquid to the cylindrical vessel in which the paddles are rotating at high speeds in the aforesaid mixer, and continuously or intermittently discharging the mixture from the vessel. The degree of mixing can be freely controlled by adjusting the amount of these materials supplied. Generally, mixing can be achieved easily even in a combination of the absorbing agent (I) and the aqueous liquid which are difficult to mix uniformly.

According to another preferred method of mixing the water-absorbing agent (I) with the aqueous liquid, the aqueous liquid is added as fine liquid droplets to the water-absorbing agent (I) by using a high-speed stirred granulator, a tumbling granulator or an air-current mixer and the mixture is stirred.

The high-speed stirred granulator denotes a granulator having a rotating blade at the bottom portion of a stirring tank, and is available under trade names Henschel Mixer (a product of Mitsui Miike Seisakusho, K. K.), New Speed Kneader (a product of Okada Seiko K. K.), and Heavy Duty Matrix (a product of Nara Kikai Seisakusho). The tumbling granulator denotes a device which tumbles the powder by the rotation or vibration of the container itself, and examples include an inclined pan-type granulator and a drum-type granulator. The gas current-type mixer denotes a device for mixing the powder by fluidizing it with a gas such as air and is available commercially under a trade name AIR-MIX (Reiborudo Kiko K.K.), for example.

The fine liquid droplets of the aqueous liquid preferably have a diameter of not more than 300 microns. If the particle diameter exceeds 300 microns, uniform dispersion of the aqueous liquid becomes difficult, and lumps of a high density are liable to form. Fine liquid droplets having a particle diameter of not more than 300 microns may be formed by using, for example, a rotating disc method, a pressurized nozzle method, or a two-fluid nozzle method. The two-fluid nozzle method is preferred because it can give liquid droplets of a very small size by a simple operation. An example of the nozzle used in this method is LUMINA (a trade name for a product of Fuso Seiki K.K.).

Spraying is most efficient and desirable for adding the fine liquid droplets of the aqueous liquid. But there is no particular restriction on the method of addition if it can achieve the addition of the aqueous liquid as fine droplets.

The water-absorbing agent (III) can be obtained by pulverizing and granulating the resulting mixture of the water-absorbing agent (I) (the mixture is in the form of granules or agglomerates) in the manner described below.

The pulverization and granulation can be performed by using ordinary pulverizing granulator such as NEW SPEED MILL (a trade name for a product of Okada Seiko K. K.), FLASH MILL (a trade name for a product of Fuji Paudal K. K.), or SPEED MILL (a trade name for a product of Showa Engineering Co., Ltd.). The pulverization and granulation may be performed immediately after mixing the water-absorbing agent (I) with the aqueous liquid, or after leaving the mixture to stand for a certain period of time.

The water-absorbing agent (III) so obtained has various advantages over the conventional known water-absorbing resins. Specifically, the water-absorbing agent (III) has high safety biologically and industrially. It can be obtained by an industrially advantageous method which does not particularly require a drying step and involves the use of an inexpensive aqueous liquid. It contains a small proportion of fine particles, and has a uniform particle size distribution. It does not significantly decrease in weight nor pollute the working environmen owing to the occurrence of dust. It has good mixability, dispersibility and flowability, and is unlikely to induce bridge formation or flushing in the hopper. Moreover, the water-absorbing agent (III) retains the excellent properties of the water-absorbing agent (I).

According to still another preferred embodiment of this invention, the water-absorbing agent (IV) is obtained by mixing the water-absorbing agent (III) with finely divided silica. This water-absorbing agent (IV) does not significantly decrease in flowability nor undergo caking upon moisture absorption, and has excellent handlability. Furthermore, it retains the excellent properties of the water-absorbing agent (III).

The finely divided silica may be the same as the finely divided silica used in obtaining the water-absorbing agent (II) from the water-absorbing agent (I).

The amount of the finely divided silica used is 0.01 to 10 parts by weight per 100 parts by weight of the water-absorbing agent (III). If the amount is less than 0.01 part by weight, no effect of addition can be observed. If the amount exceeds 10 parts by weight, no effect corresponding to the amount used can be obtained, and this is uneconomical.

Ordinary mixing methods and devices may be used to obtain the water-absorbing agent (IV) by mixing the water-absorbing agent (III) with finely divided silica, and there is no particular limitation on them.

The water-absorbing agents (I), (II), (III) and (IV) of this invention have the excellent properties described above, and can be produced industrially with good productivity. Accordingly, they can be supplied at low cost and can find a wide range of applications. For example, when they are used as absorbents for sanitary napkins, paper diapers and the like, they have the property of quickly absorbing large amounts of catamenial blood, urine or other body fluids. The absorbing ability per unit cost is much higher than in conventional products. Furthermore, since such absorbents retain the absorbed liquids even under pressure, they are comfortable to use and endure use for a long time.

The water-absorbing agents in accordance with this invention are used in the various applications mentioned above by mixing them with paper or pulp, or distributing them between substrates such as paper, pulp or a non-woven fabric, or molding them into a sheet.

The following examples illustrate the present invention in greater detail. It should be understood however that they in no way limit the scope of the present invention. In these examples, percentages and parts are by weight unless otherwise specified.

EXAMPLE 1

Four thousand parts of a 43% aqueous solution of an acrylate salt monomer composed of 74.95 mole % of sodium acrylate, 25 mole % of acrylic acid and 0.05 mole % of trimethylolpropane triacrylate was polymerized in the presence of 0.6 part of ammonium persulfate and 0.2 part of sodium hydrogen sulfite in an atmosphere of nitrogen at 55° to 80° C. to obtain a gel-like hydrous polymer. The polymer was dried in a hot air dryer at 180° C., crushed by a hammer-type crusher, and sieved on a 28-mesh wire gauze to obtain a powder that passed through the sieve (powder A). The particle size distribution of the powder A was such that the proportion of particles which passed through a 200-mesh standard sieve was 16.4 %.

One hundred parts of the powder A, 2 parts of glycerol and 2 parts of ethanol were mixed by a paddle-type mixer, and the mixture was continuously heat-treated by a paddle dryer. The average residence time in the paddle dryer was 20 minutes, and the temperature of the material at the outlet of the dryer was 190° C. As a result, a water-absorbing agent (1) was obtained. The water absorption ratios of the powder A and the waterabsorbing agent (1) and the formation of "fish-eyes" were evaluated as follows:

The resulting powder A or the water-absorbing agent (1) (0.2 g) was uniformly put into a tea bag-type bag (40 mm×150 mm) of a nonwoven fabric. The bag was dipped in 0.9% saline solution, and the weight of the bag was measured 1 minute and 10 minutes later. The weight of the bag alone after absorption was used as a blank, and the water absorption ratio of the water-absorbing agent was calculated in accordance with the following equation.

$$\text{Water absorption ratio} = \frac{\text{Weight (g) after absorption} - \text{Blank (g)}}{\text{Weight (g) of the water-absorbing agent}}$$

On the other hand, a small amount of the powder A or the absorbing agent (1) was dropped on paper wetted with water, and the formation of "fish-eyes" was observed visually.

The results are shown in Table 1. It is seen that the speed of water absorption by the water-absorbing agent (1) was much higher than that by the powder A.

COMPARATIVE EXAMPLE 1

One hundred parts of the powder A obtained in Example 1 was mixed with 2 parts of glycerin by a paddle-type mixer. The mixture was heat-treated by a paddle dryer in the same way as in Example 1 to give a comparative water-absorbing agent (1). The comparative water-absorbing agent (1) was evaluated in the same way as in Example 1.

The results are shown in Table 1. It is seen that the comparative water-absorbing agent (1) had a much higher speed of water absorption than the powder A, but a lower speed of water absorption than the water-absorbing agent (1) obtained in Example 1.

EXAMPLE 2

One hundred parts of the powder A obtained in Example 1 was mixed with 2 parts of glycerol, 4 parts of isopropanol and 4 parts of water in a twin-arm kneader. The mixture was heat-treated by a paddle dryer in the same way as in Example 1 to give a water-absorbing agent (2).

The resulting water-absorbing agent (2) was evaluated in the same way as in Example 1, and the results are shown in Table 1.

EXAMPLE 3

The powder A obtained in Example 1 was classified on a 200-mesh standard sieve to obtain particles which passed through the sieve and particles which remained on the sieve. The particles which passed through the sieve and those which remained on it were mixed in a weight ratio of 2:1 to obtain a powder B which contained 66.7 % by weight of the particles which passed through the 200-mesh standard sieve.

One hundred parts of the powder B was mixed with 2 parts of glycerol, 4 parts of isopropanol and 4 parts of water, and the mixture was heat-treated, in the same way as in Example 2 to give a water-absorbing agent (3). The water-absorbing agent (3) was evaluated in the same way as in Example 1. The results are shown in Table 1.

EXAMPLE 4

Three hundred parts of cyclohexane was taken into a reactor, and 1.8 parts of sorbitan monostearate was dissolved in it. An aqueous monomer solution obtained by dissolving 30 parts of acrylic acid in 40 parts of water, neutralizing the solution with 12.5 parts of sodium hydroxide and dissolving 0.05 part of potassium persulfate was dispersed in the resulting solution and polymerized for 5 hours at 65° C. in a stream of nitrogen. After the polymerization, the product was dried under reduced pressure, and sieved on a 28-mesh wire gauze to obtain a powder C which passed through the 28-mesh wire gauze.

One hundred parts of the powder C was mixed with 3 parts of trimethylolpropane, 2 parts of ethanol and 4 parts of dioxane by a V-type mixer. The mixture wa placed in a thin layer on a belt conveyor and passed through an infrared ray dryer to heat-treat it and obtain a water-absorbing agent (4). The average heating time was 10 minutes, and the temperature of the material at the outlet of the dryer was 193° C.

The powder C and the water-absorbing agent (4) were evaluated in the same way as in Example 1, and the results are shown in Table 1.

COMPARATIVE EXAMPLE 2

After the same polymerization as in Example 3 was carried out, water was evaporated by azeotropic distillation to adjust the amount of water in the water-absorbing resin particles suspended in cyclohexane to 42.9 parts (water content 30 % by weight) per 100 parts by weight of the water-absorbing resin. Then, a solution of 1.1 g (corresponding to 3 parts per 100 parts by weight of the water-absorbing resin) of trimethylolpropane in 2 g of water was added at 73° C., and the mixture was maintained at this temperature for 2 hours. The water-absorbing resin particles were collected from the slurry by filtration, dried under reduced pressure at 80° C., and sieved on a 28-mesh wire gauze to obtain a comparative water-absorbing agent (2) which passed through the 28-mesh wire gauze.

The comparative water-absorbing agent (2) was evaluated in the same way as in Example 1, and the results are shown in Table 1.

COMPARATIVE EXAMPLE 3

One hundred parts of the powder C obtained in Example 4 was taken into a reactor, and 125 parts of methanol was added. With stirring, a solution of 3 parts of trimethylolpropane in 25 parts of water was added and mixed. The reactor was then maintained in an oil bath at 110° C. to dry the contents and to obtain a comparative water-absorbing agent (3). More than 1 hour was needed for drying.

The comparative water-absorbing agent (3) was evaluated in the same way as in Example 1, and the results are shown in Table 1.

EXAMPLE 5

Three grams of each of the powder A and the water-absorbing agent (1) obtained in Example 1, the comparative water-absorbing agent (1) obtained in Comparative Example 1, the water-absorbing agent (2) obtained in Example 2, the powder B and the water-absorbing agent (3) obtained in Example 3 and the powder C and the water-absorbing agent (4) obtained in Example 4 was uniformly distributed over a baby paper diaper (composed of a nonwoven cloth, a cotton-like pulp, water-absorbing paper and a waterproof film and having a weight of 72 g), and 100cc of 0.9% saline solution was added to the paper diaper. After standing at room temperature for 10 minutes, ten paper towels (23 cm×23 cm) were folded in two and laid over the paper diaper. A weight of 10 kg was placed on the towel assembly, and the entire assembly was left to stand for 1 minute. Then, the amount of saline solution which migrated to the paper towels was measured. The results are shown in Table 1.

way as in Examples 1 and 5. The results are shown in Table 2.

These results demonstrate that the granulated water-absorbing agent (5) had a greatly decreased amount of fine particles, and the occurrence of dust was not noted, and that it retained the excellent properties of the starting water-absorbing agent (1).

EXAMPLE 7

The water-absorbing agent (2) obtained in Example 2 was charged into HEAVY DUTY MATRIX (made by

TABLE 1

|  | (*) | Water absorption ratio after | | Amount of 0.9% saline solution that migrated (g) | Formation of "fish-eyes" (**) |
|---|---|---|---|---|---|
|  |  | 1 min. | 10 min. |  |  |
| Ex. 1 | Powder A | 30 | 52 | 25.2 | X |
|  | Water-absorbing agent (1) | 55 | 67 | 2.3 | O |
| CEx. 1 | Comparative water-absorbing agent (1) | 45 | 61 | 8.5 | O |
| Ex. 2 | Water-absorbing agent (2) | 53 | 65 | 1.8 | O |
| Ex. 3 | Powder B | 21 | 39 | — | X |
|  | Water-absorbing agent (3) | 47 | 63 | 5.4 | O |
| Ex. 4 | Powder C | 20 | 33 | — | X |
|  | Water-absorbing agent (4) | 48 | 63 | 2.2 | O |
| CEx. 2 | Comparative water-absorbing agent (2) | 40 | 45 | — | Δ |
| CEx. 3 | Comparative water-absorbing agent (3) | 42 | 47 | — | O |

(*) Ex. = Example, CEx. = Comparative Example
(**) The evaluation was on the following standard.
O No "fish-eyes" formed.
Δ "fish-eyes" did not easily form.
X "fish-eyes" formed.

As is clear from the results shown in Table 1, the water-absorbing agents in accordance with this invention do not form "fish-eyes", and have a high speed of water absorption, and that the water-absorbing agents of this invention have high water retentivity even under pressure.

The water-absorbing agents of this invention have higher speeds of water absorption and higher water retentivity under pressure than the comparative water-absorbing agent (1) obtained by adding only the polyhydric alcohol.

EXAMPLE 6

Three parts of water was added dropwise to 100 parts of the water-absorbing agent obtained in Example 1, and the mixture was stirred, by using SAND TURBO (a trade name for a product of Hosokawa Micron Co., Ltd.). The mixture was crushed and granulated by using FLASH MILL (a trade name for a product of Fuji Paudal K. K.) to obtain a water-absorbing agent (5).

The particle size distributions of the waterabsorbing agent (5) and the water-absorbing agent (1) were measured by using a vibratory sieve.

The water absorption ratio and the amount of saline solution that migrated were also measured in the same way as in Example 6. The results are shown in Table 2.

Nara Kikai Seisakusho K. K.), and with stirring, water in an amount of 4 parts per 100 parts of the water-absorbing agent was sprayed as fine droplets through a 2-fluid nozzle onto the water-absorbing agent (2). The average diameter of the liquid droplets was about 100 microns. The mixture was crushed and granulated by FLASH MILL (made by Fuji Paudal K. K.) to obtain a water-absorbing agent (6).

The particle size distributions of the water-absorbing agent (6) and the water absorbing agent (2) were measured by a vibratory sieve. The water absorption ratio and the amount of saline solution that migrated were measured in the same way as in Example 6. The results are shown in Table 2.

COMPARATIVE EXAMPLE 4

A comparative water-absorbing agent (4) in the granulated state was obtained in the same way as in Example 7 except that water was supplied as relatively large droplets having a diameter of 1 to 2 mm to the water-absorbing agent (2) obtained in Example 2. The particle size distribution of the comparative water-absorbing agent (4) was measured in the same way as in Example 7, and the results are shown in Table 2.

TABLE 2

|  |  | Particle size distribution (*) | | | | | Water absorption ratio (after 10 min.) | Amount of saline solution that migrated (g) |
| --- | --- | --- | --- | --- | --- | --- | --- | --- |
|  |  | 28 on | 28–48 | 48–100 | 100–200 | 200 pass |  |  |
| Ex. 6 | Water-absorbing agent (1) | — | 25.1 | 36.4 | 22.1 | 16.4 | 67 | 2.3 |
|  | Water-absorbing agent (5) | 0.4 | 46.0 | 40.3 | 12.2 | 1.1 | 65 | 2.2 |
| Ex. 7 | Water-absorbing agent (2) | 0.1 | 29.5 | 35.8 | 24.5 | 10.1 | 65 | 1.8 |
|  | Water-absorbing agent (6) | 0.4 | 45.8 | 42.7 | 10.5 | 0.6 | 63 | 1.7 |
| CEx. 4 | Comparative Water-absorbing agent (4) | 17.8 | 21.4 | 36.1 | 18.5 | 6.2 | — | — |

(*) 28 on = the weight percent of particles which remained on a 28-mesh wire gauze
28–48 = the weight percent of particles which passed the 28-mesh wire gauze but remained on a 48-mesh wire gauze
48–100 = the weight percent of particles which passed through the 48-mesh wire gauze but remained on a 100-mesh wire gauze
100–200 = the weight percent of particles which passed through the 100-mesh wire gauze but remained on a 200-mesh wire gauze
200 pass = the weight percent of particles which passed through the 200-mesh wire gauze The results given in Table 2 demonstrate that the granular water-absorbing agent produced by adding the aqueous liquid to the powdery water-absorbing agent, stirring them, and crushing and granulating the resulting mixture has a small content of fine particles and a uniform particle size distribution, does not generate dust, and retains the properties of the starting powdery water-absorbing agent.

EXAMPLE 8

One hundred parts of the water-absorbing agent (1) obtained in Example 1 was mixed with 2 parts of finely divided silica ("Aerosil 200", a trade name for a product of Aerosil Co., Ltd.) by a V-type mixer to obtain a water-absorbing agent (7).

One gram of the water-absorbing agent (7) was put in a petri dish having a diameter of 100 mm, and left to stand at 20° C. and 65% RH. The petri dish was tilted by hand, and the time which elapsed until the powder lost flowability was measured. Furthermore, the water absorption ratio of the water-absorbing agent (7) and the amount of saline solution that migrated were determined in the same way as in Examples 1 and 5. The results are shown in Table 3.

EXAMPLE 9

Water-absorbing agents (8) and (9) were obtained by mixing 100 parts each of the water-absorbing agents (5) and (6) obtained in Examples 6 and 7 with 3 parts and 5 parts, respectively, of finely divided silica (CARPLEX® #67, a trade name for a product of Shionogi & Co., Ltd.) in the same way as in Example 8.

The water-absorbing agents (8) and (9) were evaluated in the same way as in Example 8, and the results are shown in Table 3.

TABLE 3

|  |  | Flow-ability retention time (hours) | Water absorption ratio after | | Amount of saline solution that migrated (g) |
| --- | --- | --- | --- | --- | --- |
|  |  |  | 1 min. | 10 min. |  |
| Ex. 8 | Water-absorbing agent (1) | 2 | 55 | 67 | 2.3 |
|  | Water-absorbing agent (7) | 36 | 56 | 68 | 2.3 |
| Ex. 9 | Water-absorbing agent (5) | 2 | 53 | 65 | 2.2 |
|  | Water-absorbing agent (6) | 2 | 52 | 63 | 1.7 |

TABLE 3-continued

|  | Flow-ability retention time (hours) | Water absorption ratio after | | Amount of saline solution that migrated (g) |
| --- | --- | --- | --- | --- |
|  |  | 1 min. | 10 min. |  |
| Water-absorbing agent (8) | 38 | 55 | 67 | 2.1 |
| Water-absorbing agent (9) | 45 | 53 | 65 | 1.7 |

The results given in Table 3 demonstrate that the water-absorbing agents obtained by mixing the powdery water-absorging agents with finely divided silica do not significantly decrease in flowability nor undergo caking upon moisture absorption and have excellent handlability, and that they retain the excellent properties of the original powdery water-absorbing agents.

What is claimed is:

1. In a water-absorbing agent comprising a water-absorbing resin powder having the molecular chains near its durface crosslinked, said resin powder being obtained by mixing 100 parts by weight of a powder of a carboxyl-containing water-absorbing resin selected from the group consisting of a hydrolyzate of a starch-acrylonitrile graft polymer, a partially neutralized product of a starch-acrylic acid graft polymer, a saponification product of a vinyl acetate-acrylic ester copolymer, a hydrolyzate of an acrylonitrile copolymer, a crosslinked product of a hydrolyzate of an acrylonitrile copolymer, a hydrolyzate of an acrylamide copolymer, a crosslinked product of a hydrolyzate of an acrylamide copolymer, a partially neutralized product of polyacrylic acid, and a crosslinked product of partially neutralized polyacrylic acid with 0.001 to 10 parts by weight of a polyhydric alcohol and heating the mixture at a temperature of at least 90° C. to react the powder of a carboxyl-containing water-absorbing resin with the polyhydric alcohol, the improvement comprising conducting the mixing of said powder of a carboxyl-containing water-absorbing resin and said polyhydric alcohol in the presence of 0.01 to 8 parts by weight of a hydrophilic organic solvent and 0 to 8 parts by weight of water.

2. The water-absorbing agent of claim 1 wherein the proportion of water is 0 to 5 parts by weight.

3. The water-absorbing agent of claim 2 wherein the proportion of water is 0.5 to 4 parts by weight.

4. The water-absorbing agent of any one of claims 1 or 3 wherein the carboxyl-containing water-absorbing resin is an alkali metal acrylate-type polymer obtained by copolymerizing 100 parts by weight of an acrylic acid salt-type monomer comprising 1 to 50 mole % of acrylic acid and 50 to 99 mole % of an alkali metal acrylate and 0 to 5 parts by weight of a crosslinkable monomer in aqueous solution in a monomer concentration of at least 20% by weight, and heat-drying the resulting gel-like hydrous polymer.

5. The water-absorbing agent of any one of claims 1 or 3 wherein the water-absorbing resin powder has such a particle size that the proportion of particles which pass through a 200-mesh standard sieve is not more than 50 % by weight.

6. A water-absorbing agent obtained by mixing 100 parts by weight of the water-absorbing agent of claim 1 with 0.01 to 10 parts by weight of finely divided silica.

7. The water-absorbing agent of claim 6 wherein the proportion of water is 0 to 5 parts by weight.

8. The water-absorbing agent of claim 7 wherein the proportion of water is 0.5 to 4 parts by weight.

9. The water-absorbing agent of any one of claims 6 or 8 wherein the carboxyl-containing water-absorbing resin is an alkali metal acrylate-type polymer obtained by copolymerizing 100 parts by weight of an acrylic acid salt-type monomer comprising of 1 to 50 mole % of acrylic acid and 50 to 99 mole % of an alkali metal acrylate and 0 to 5 parts by weight of a crosslinkable monomer in aqueous solution in a monomer concentration of at least 20 % by weight, and heat-drying the resulting gel-like hydrous polymer.

10. The water-absorbing agent of any one of claims 6 or 8 wherein the water-absorbing resin powder has such a particle size that the proportion of particles which pass through a 200-mesh standard sieve is not more than 50% by weight.

11. A water-absorbing agent obtained by adding an aqueous liquid to the water-absorbing agent of claim 1, stirring them, and pulverizing and granulating the resulting mixture.

12. The water-absorbing agent of claim 11 which is obtained by performing the stirring by a high-speed rotating paddle-type mixer.

13. The water-absorbing agent of claim 11 which is obtained by performing the stirring by a high-speed agitating type granulator, a tumbling granulator or a gas current-type mixer, and adding the aqueous liquid as fine liquid droplets having a particle diameter of not more than 600 microns.

14. The water-absorbing agent of claim 13 wherein the aqueous liquid is added as droplets having a particle diameter of not more than 300 microns.

15. The water absorbing agent of claim 11 which is obtained by adding 1 to 30 parts of the aqueous liquid to 100 parts by weight of the water-absorbing resin.

16. The water-absorbing agent of claim 11 wherein the powder is obtained by adding 0 to 5 parts by weight of water.

17. The water-absorbing agent of any one of claims 11 or 15 wherein the powder is obtained by using 0.5 to 4 parts by weight of water.

18. The water-absorbing agent of any one of claims 11 or 15 wherein the carboxyl-containing water-absorbing resin is an alkali metal acrylate-type polymer obtained by copolymerizing 100 parts by weight of an acrylic acid salt-type monomer comprising 1 to 50 mole % of acrylic acid and 50 to 99 mole % of an alkali metal acrylate and 0 to 5 parts by weight of a crosslinkable monomer in aqueous solution in a monomer concentration of at least 20 % by weight, and heat-drying the resulting gel-like hydrous polymer.

19. The water-absorbing agent of any one of claims 11 or 15 wherein the water-absorbing resin powder has such a particle size that the proportion of particles which pass through a 200-mesh standard sieve is not more than 50 % by weight.

20. A water-absorbing agent obtained by mixing 100 parts by weight of the water-absorbing agent of claim 11 with 0.01 to 10 parts by weight of finely divided silica.

21. The water-absorbing agent of claim 20 which is obtained by using 0 to 5 parts by weight of water.

22. The water-absorbing agent of claim 21 which is obtained by using 0.5 to 4 parts by weight of water.

23. The water-absorbing agent of any one of claims 20 or 22 wherein the carboxyl-containing water-absorbing resin is an alkali metal acrylate-type polymer obtained by copolymerizing 100 parts by weight of an acrylic acid salt-type monomer comprising 1 to 50 mole % of acrylic acid and 50 to 99 mole % of an alkali metal acrylate and 0 to 5 parts by weight of a crosslinkable monomer in aqueous solution in a monomer concentration of at least 20 % by weight, and heat-drying the resulting gel-like hydrous polymer.

24. The water-absorbing agent of any one of claims 20 or 22 wherein the water-absorbing resin powder has such a particle size that the proportion of particles which pass through a 200-mesh standard sieve is not more than 50% by weight.

25. The water-absorbing agent of claim 4 wherein the water-absorbing resin powder has such a particle size that the proportion of particles which pass through a 200-mesh standard sieve is not more than 50% by weight.

26. The water-absorbing agent of claim 9 wherein the water-absorbing resin powder has such a particle size that the proportion of particles which pass through a 200-mesh standard sieve is not more than 50% by weight.

27. The water-absorbing agent of claim 18 wherein the water-absorbing resin powder has such a particle size that the proportion of particles which pass through a 200-mesh standard sieve is not more than 50% by weight.

28. The water-absorbing agent of claim 23 wherein the water-absorbing resin powder has such a particle size that the proportion of particles which pass through a 200-mesh standard sieve is not more than 50% by weight.

29. The water-absorbing agent of claim 1 wherein the hydrophilic organic solvent is selected from the group consisting of lower alcohols, ketones, ethers, amides and sulfoxides.

30. The water-absorbing agent of claim 1 wherein the hydrophilic organic solvent is selected from the group consisting of methyl alcohol, ethyl alcohol, n-propyl alcohol, isopropyl alcohol, n-butyl alcohol, isobutyl alcohol, t-butyl alcohol, acetone, dioxane, tetrahydrofuran, N,N-dimethyl-formamide and dimethyl sulfoxide.

31. The water-absorbing agent of claim 1 wherein the proportion of hydrophilic organic solvent is 0.1 to 6 parts by weight.

32. The water-absorbing agent of claim 4 obtained by mixing 100 parts by weight of said carboxyl-containing water-absorbing resin with 2 parts of glycerol and 2 parts of ethanol and heat treating the mixture.

33. The water absorbing agent of claim 4 obtained by mixing 100 parts by weight of said carboxyl-containing water-absorbing resin with 2 parts of glycerol, 4 parts of isopropanol and 4 parts of water and heat treating the mixture.

34. The water-absorbing agent of claim 6 wherein the proportion of hydrophilic organic solvent is 0.1 to 6 parts by weight.

35. The water-absorbing agent of claim 11 wherein the proportion of hydrophilic organic solvent is 0.1 to 6 parts by weight.

36. The water-absorbing agent of claim 20 wherein the proportion of hydrophilic organic solvent is 0.1 to 6 parts by weight.

37. The water absorbing agent of claim 6 wherein the hydrophilic organic solvent is selected from the group consisting of lower alcohols, ketones, ethers, amides and sulfoxides.

38. The water absorbing agent of claim 11 wherein the hydrophilic organic solvent is selected from the group consisting of lower alcohols, ketones, ethers, amides and sulfoxides.

39. the water absorbing agent of claim 20 wherein the hydrophilic organic solvent is selected from the group consisting of lower alcohols, ketones, ethers, amides and sulfoxides.

* * * * *